United States Patent [19]
Kemp et al.

[11] Patent Number: 5,536,656
[45] Date of Patent: Jul. 16, 1996

[54] PREPARATION OF TISSUE EQUIVALENTS BY CONTRACTION OF A COLLAGEN GEL LAYERED ON A COLLAGEN GEL

[75] Inventors: Paul Kemp, Cambridge; Eugene Bell, Boston; David T. Kagan, Brookline; Valerie Mason, Acton; John Cavallaro, Lexington, all of Mass.

[73] Assignee: Organogenesis, Inc., Canton, Mass.

[21] Appl. No.: 193,809

[22] Filed: Feb. 9, 1994

Related U.S. Application Data

[63] Continuation of Ser. No. 408,052, Sep. 15, 1989, abandoned.

[51] Int. Cl.$^6$ ................. C12N 5/00; C12M 3/04; A61F 13/00; A61F 2/00
[52] U.S. Cl. ............... 435/240.23; 424/422; 424/423; 435/240.2; 435/1.1
[58] Field of Search .................. 435/177, 180, 435/240.2, 240.23, 240.243, 285; 623/1; 424/422, 423

[56] References Cited

U.S. PATENT DOCUMENTS

| | | | |
|---|---|---|---|
| 2,677,646 | 5/1954 | Lovell et al. | 435/297 |
| 2,761,813 | 9/1956 | Goetz | 435/301 |
| 4,290,911 | 9/1981 | Cook et al. | 252/316 |
| 4,312,739 | 1/1982 | Hansson et al. | 252/316 |
| 4,485,096 | 11/1984 | Bell | 424/94 |
| 4,485,097 | 11/1984 | Bell | 424/95 |
| 4,505,266 | 3/1985 | Yannas et al. | 128/1 R |
| 4,539,716 | 9/1985 | Bell | 623/1 |
| 4,546,500 | 10/1985 | Bell | 623/1 |
| 4,556,056 | 12/1985 | Fischer et al. | 128/156 |
| 4,578,354 | 3/1986 | Cannon | 435/178 |
| 4,598,045 | 7/1986 | Masover et al. | 435/34 |
| 4,604,346 | 9/1987 | Bell et al. | 435/1 |
| 4,734,372 | 3/1988 | Rotman | 435/287 |
| 4,735,832 | 4/1988 | Ichikawa et al. | 428/451 |
| 4,835,102 | 5/1989 | Bell et al. | 435/284 |
| 4,837,379 | 6/1989 | Weinberg | 424/101 |
| 4,912,057 | 3/1990 | Guirguis et al. | 435/285 |
| 4,963,489 | 10/1990 | Naughton et al. | 435/240.1 |
| 4,996,154 | 2/1991 | Gabriels | 435/240.23 |
| 5,026,649 | 6/1991 | Lyman et al. | 435/284 |
| 5,032,508 | 7/1991 | Naughton et al. | 435/32 |
| 5,037,656 | 8/1991 | Pitt et al. | 435/240.2 |

FOREIGN PATENT DOCUMENTS

| | | |
|---|---|---|
| 285474 | 10/1988 | European Pat. Off. . |
| 285471 | 10/1988 | European Pat. Off. . |
| 358506 | 3/1990 | European Pat. Off. . |

OTHER PUBLICATIONS

Effects of Human Recombinant Interferons—, —and —on Growth and Survival of Human Cancer Nodules Maintained in Continuous Organotypic Culture. R. Beaupain et al., Eur J Cancer Clin Oncol, vol. 22, No. 2, pp. 141–149, 1986.

Three-dimensional culture of human keratinocy on a dermal equivalent as a model system to study environmental modulation of epiderms physiology in vitre: effect of air–exposure, D. Asselineau et al., British Journal of Dermatology (1986) 115, Supplement 31, 126–127.

Characterization of Rat Ventral Prostatic Epithelial Cells in Collogen Gel Culture, Terence O'Connor et al., The Prostate 7:305–319 (1985).

Metabolic Cooperation between Mouse Mammary Tumor Subpopulations in Three—Dimensional Collagen Gel Cultures, Bonnie E. Miller et al., Cancer Research 46, 89–93, Jan. 1986.

Factors Affecting Growth and Drug Sensitivity of Mouse Mammary Tumor Lines in Collagen Gel Cultures, Bonnie E. Miller et al., Cancer Research 45,4200–4205, Sep. 1985.

Resistance of V79 Multicell Spheroids to Mitoxantrone: Drug Uptake and Cytotoxicity, Tewfik J. Bichay et al., Cancer Drug Delivery, vol. 4, Nov. 1987, Mary Ann Liebert, Inc., Publishers.

Cell Aggregates —A New In Vitro Model System of Tumor Growth, Philip J. DiSaia, MD, et al., Gynecologic Oncology 1, 363–369 (1973).

Vaughan et al. "Growth and Differentiation of Primary Rat Keratinocytes on Synthetic Membranes." In Vitro Cellular & Developmental Biology, vol. 22, No. 3, (Mar. 1986), pp. 141–149.

*Primary Examiner*—David M. Naff
*Attorney, Agent, or Firm*—David G. Conlin; Linda M. Buckley

[57] ABSTRACT

Tissue equivalents are produced by applying a solution of collagen without cells to a permeable membrane, gelling to produce a collagen gel on the membrane, applying a mixture of collagen and a contractile agent to the collagen gel, gelling the mixture and allowing the resultant gel to undergo radial contraction which is controlled by the collagen gel on the membrane. A suitable contractile agent is fibroblast cells. A skin tissue equivalent is produced by disposing human epidermal cells on the contracted collagen gel and allowing epidermalization to occur. A nutrient medium can be supplied to the cells. An absorbent member may be disposed adjacent the permeable membrane opposite the collagen gel on the membrane. The permeable membrane can be the bottom of an inner well disposed in an outer well for containing a nutrient medium in contact with the membrane. The nutrient medium may be contained in the outer well in an agarose gel in contact with the membrane.

22 Claims, 3 Drawing Sheets

PREPARATION OF TISSUE EQUIVALENTS BY CONTRACTION OF A COLLAGEN GEL LAYERED ON A COLLAGEN GEL

This is a continuation of application Ser. No. 07/408,052 filed on Sep. 15, 1989, now abandoned.

FIELD OF THE INVENTION

This invention relates to methods of preparing and using tissue equivalents comprising (i) a hydrated collagen lattice contracted by a contractile agent, and (ii) hydrated collagen gel in contact with a permeable member. This invention further relates to test systems incorporating such tissue equivalents.

Tissue equivalents comprising a hydrated collagen lattice contracted by a contractile agent, such as fibroblast cells or blood platelets, to form the tissue equivalent are disclosed in U.S. Pat. Nos. 4,485,096; 4,485,097; 4,539,716; 4,546,500; 4,604,346; and 4,837,379, and copending U.S. patent application Ser. No. 07/252,249, filed Sep. 30, 1988, all of which are incorporated herein by reference (hereinafter collectively referred to as "the Patents"). Tissue as used herein comprises any group or layer of cells which together perform one or more certain functions. Such tissue equivalents include, but are not limited to, equivalents of epithelial tissue, connective tissue, cartilage, bone, organs, glands and blood vessels and comprise living cells and extracellular matrix molecules, principally collagen, and may optionally be provided with components not typically found in normal tissue.

In general such living tissue equivalents are produced by forming a hydrated collagen lattice which is contracted into a living tissue. Examples of contractile agents include fibroblasts cells, smooth muscle cells and blood platelets. A skin-equivalent can be produced from the living connective tissue equivalent substrate by plating keratinocyte cells thereon and providing for their growth.

The aforementioned tissue equivalents are populated with cells that can remain alive for long periods of time and can be produced in quantity with the assurance that the units produced will be essentially uniform. Cells in such tissue equivalents resemble cells of normal tissue in their structural arrangement, in their biosynthetic output, and in their permeability. It should be understood that these tissue equivalents need not be human but may be those of any animal as desired.

Tissue equivalents in accordance with the teachings of the present invention have a broad range of applications including applications in research and development, tissue and organ replacement and testing.

Human skin tissue equivalents permit the growth of normal human epidermal cells that differentiate fully which have not, to date, been obtained by routine culture methods. Such skin tissue equivalents have been extensively used as a permanent skin replacement in animal experiments. The morphological appearance of such skin tissue equivalent is normal, constituent cells persist after grafting as shown by genetic marking, and functional performance has been demonstrated. See, e.g., *Science,* 211: 1052–1054 (1981); *J. Invest. Dermatol.* 81: 2s–10s (1983).

Skin tissue equivalents fabricated in vitro by the methods disclosed in the Patents bear a close resemblance to natural skin. Such equivalents comprise a multilayered epidermis with well-developed basal cells joined to a dermal layer. The dermal layer comprises a collagen matrix in which dermal fibroblasts are distributed. Cells in the three-dimensional collagen matrix achieve a state of differentiation in many respects similar to that which prevails in vivo. For example, resident fibroblasts are synthetically active and enrich the matrix in vitro both with collagen, and a number of other molecular species, and exhibit permeability properties typical of a cell in vivo. See, e.g., *Collagen Rel. Res.* 4: 351–364 (1984). Furthermore, skin tissue equivalents can be pigmented by inclusion of melanocytes that donate pigment to keratinocytes and it has been shown that the process is speeded up in vitro by ultraviolet radiation (*J. Invest. Dermatol.* 87: 642–647, 1986).

U.S. Pat. No. 4,835,102 discloses systems incorporating tissue equivalents that reproduce in vitro many of the physical and biological characteristics of natural tissues and are useful for the study of, for example, tissue cell biology, physiology and pathology. Such systems include apparatus, and kits for determining the interaction of tissue and at least one agent by use of at least one tissue equivalent. Agent includes, but is not limited to, various substances such as chemicals, cosmetics, pharmaceuticals; stimuli, e.g., light or physical injury; and tissue protective agents.

Tissue equivalents can be cast in any desired shape. Skin tissue equivalents for use in skin grafts and in test systems are generally cast as flat sheets and blood vessel equivalents are generally fabricated as a hollow tube or a network of hollow tubes. However, the natural geometry or configuration of the tissue equivalent may be changed if desired. For example, skin tissue equivalent may be cast as a cylinder rather than as a sheet.

When fibroblast or smooth muscle cells are used as the contractile agent in the production of tissue equivalents, an unrestrained collagen lattice will typically undergo contraction in all dimensions. Various methods to assist in forming living tissue and tissue equivalents having controllable configurations and/or dimensions are disclosed in the Patents, e.g., U.S. Pat. No. 4,485,096. For example, a collagen lattice may be cast on a stainless steel frame to hold the borders fixed and thus to contract substantially only in the thickness dimension. Other materials which may be used to control the configuration of the tissue equivalent include VELCRO® Hook and Loop Fasteners, a trademark of Velcro Corporation, textured plastics and textured TEFLON® PTFE Polytetrafluoroethylene, a trademark of E.I. Du Pont de Nemours and Company. Although these constraining means are effective, it is preferable in many instances, both in terms of cost and simplicity, to employ constraining means which are not intergral with the casting chamber.

In light of the many applications of tissue equivalents, improved tissue equivalents and methods of making such tissue equivalents are being sought.

SUMMARY OF THE INVENTION

Figure 1:
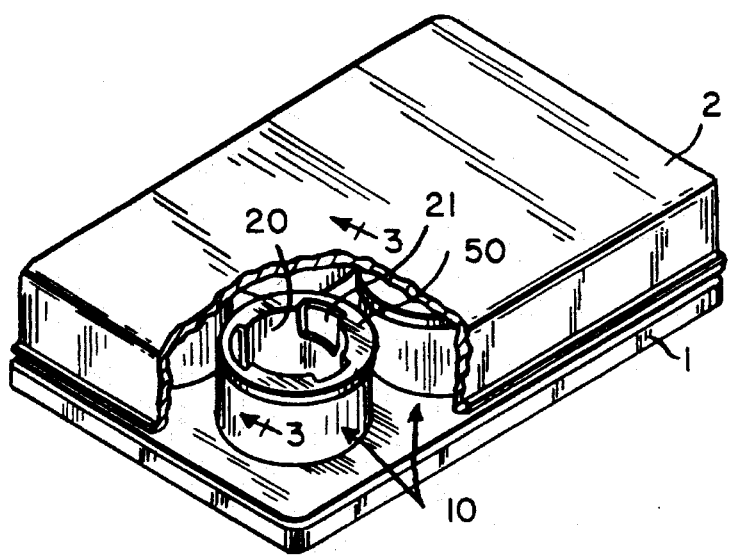
FIG. 1 is an isometric view, partially broken away, of one apparatus according to the present invention.

The present invention provides tissue equivalents comprising (i) a hydrated collagen lattice contracted by a contractile agent, and (ii) a hydrated collagen gel. The present invention also provides tissue equivalents having improved properties including, increased reproducibility from sample to sample in the degree of contraction and, in the case of skin tissue equivalents, in the degree of differentiation of the epidermis.

In some embodiments of the present invention, such tissue equivalents are adjacent to one or more absorbent members including fibrous pads and gels such as agarose.

The present invention also provides methods of making and using such improved tissue equivalents. The methods taught herein also offer advantages over those methods disclosed in the Patents in terms of ease of fabrication and reduced costs of manufacture.

One method in accordance with the present invention whereby a tissue equivalent is formed comprises:

(a) forming a mixture comprising collagen and at least one contractile agent; and (b) applying the mixture obtained in step (a) to an acellular, hydrated collagen gel, and maintaining the mixture and gel under conditions which permit formation of the tissue equivalent.

The present invention also provides apparatus incorporating such tissue equivalents for determining the interaction of tissue and one or more agents.

In one preferred embodiment of the present invention such apparatus comprises a first and a second region defined by a permeable means provided with a hydrated collagen gel on which a tissue equivalent is disposed, whereby the tissue equivalent defines the first region and the permeable member defines the second region.

In yet another preferred embodiment such apparatus comprises at least one tissue equivalent and at least one container for the tissue equivalent, the container comprising:

(i) an inner well comprising a permeable means provided with an acellular, hydrated collagen gel on which the tissue equivalent is disposed, whereby the permeable means defines the bottom of the inner well, and (ii) an outer well within which the inner well is disposed.

DETAILED DESCRIPTION OF THE INVENTION

The tissue equivalents of the present invention, although similar in both methods of preparation and use to those comprising a hydrated collagen lattice as disclosed in the Patents, further comprise a layer of collagen.

It has been unexpectedly discovered that a collagen lattice cast on an acellular, hydrated collagen gel in contact with a permeable member does not undergo substantial radial or lateral contraction while contracting in the thickness dimension, thus eliminating the need to anchor the collagen lattice on, e.g., a stainless steel frame, to control radial or lateral contraction. By way of an example, a 24 mm diameter collagen lattice cast as taught in the Patents, but without an anchoring means, would contract radially to a diameter of 5 mm or less. In contrast, a 24 mm diameter collagen lattice cast on an acellular, hydrated collagen gel in contact with a permeable member will typically contract radially to a diameter of about 15 mm. The elimination of the anchoring means to control lateral/radial contraction offers advantages in terms of cost reduction and ease of fabrication of tissue equivalents. It should be understood that such anchoring means can be used in conjunction with hydrated collagen gel in contact with a permeable member if desired.

One method of obtaining the tissue equivalents of present invention comprises:

(a) forming a mixture comprising collagen and at least one contractile agent; and (b) applying the mixture obtained in step (a) to an acellular, hydrated collagen gel in contact with a permeable member, and maintaining the mixture and gel under conditions which permit formation of the tissue equivalent.

In some embodiments of the present invention, one or more absorbent members, including but not limited to, fibrous pads, cotton pads and gels, agarose, are used in conjunction with the collagen gel described above. Such absorbent members have been found to provide a consistent and level physical support and to promote uniform contact between the tissue equivalent and the cell culture medium. Typically, the absorbent member is adjacent to the surface of the collagen gel opposite the hydrated collagen lattice. Where the absorbent member(s) is itself a gel, e.g., agarose, the gel may be provided together with a nutrient media to provide nutrients to the tissue equivalent.

The following experimental endpoints have been monitored in tissue equivalents maintained with and without the hydrated collagen gel and/or the absorbent member during various phases of development of a skin tissue equivalent:

1. Glucose utilization;

2. The extent and quality of epidermal stratification and cornification;

3. pH of medium.

The observed pH of media obtained from tissue equivalents maintained with the absorbent member(s) were consistently higher, and closer to physiological pH than tissue equivalents maintained in the absence of these members. In addition, glucose utilization was observed to be generally lower in tissue equivalents maintained with the absorbent member.

It has surprisingly been found that mature cornification is promoted in skin tissue equivalents made by use of the absorbent member(s) compared to control skin equivalents made without such members. Although the mechanism by which these absorbent members may influence epidermal differentiation is unknown, it is postulated that such members may act as diffusion barriers, e.g., a permeability barrier, and may filter the medium and/or to retain secreted cellular products in close proximity to the tissue equivalents.

Living skin equivalents of the present invention are prepared as described in the Patents, except that in accordance with the present invention, the hydrated collagen lattice is cast on an acellulor, hydrated collagen gel.

One method of producing a skin tissue equivalent in accordance with the present invention comprises:

(a) forming a mixture comprising collagen and at least one contractile agent;

(b) applying the mixture obtained in step (a) to an acellulor, hydrated collagen gel in contact with a permeable member, and maintaining the mixture and gel under conditions which permit formation of the tissue equivalent; and (c) seeding the tissue equivalent obtained in step (b) with keratinocytes.

By way of background, one convenient protocol for casting the tissue equivalents of the present invention, involves rapidly mixing together an acidic solution of collagen having a pH of about 3 to 4, with nutrient media, adjusting the pH of the resultant solution, if necessary, to about pH 6.6 to pH 7.8, adding fibroblast cells, transferring the resultant mixture (the "casting mixture") into an appropriate mold or casting device having an acellulor, hydrated collagen gel disposed therein and, then, incubating at a temperature preferably about 35° to 38° C. It is most convenient to adjust pH and combine the ingredients of the casting mixture simultaneously. However, these steps may be carried out in any desired order, provided that the steps are completed so that the casting mixture can be transferred to a mold for appropriate setting. The collagen fibrils precipitate from the casting mixture as a result of warming the solution and raising the pH to form a hydrated collagen gel contracted by a contractile agent and disposed on hydrated collagen gel.

Although the methods of making living tissue provided by the present invention are applicable to the fabrication of tissue equivalents in general, these methods will be illustrated in connection with the production of skin equivalents for use in skin grafting applications and in test systems incorporating skin equivalents.

Apparatus for, methods of, and kits for determining the interaction of tissues and one or more agents by use of tissue equivalents, including skin tissue equivalents, are described in U.S. Pat. No. 4,835,102. Tissue equivalents for such applications may also advantageously further comprise, in accordance with the present invention, a collagen gel in contact with a permeable member.

Figure 2:
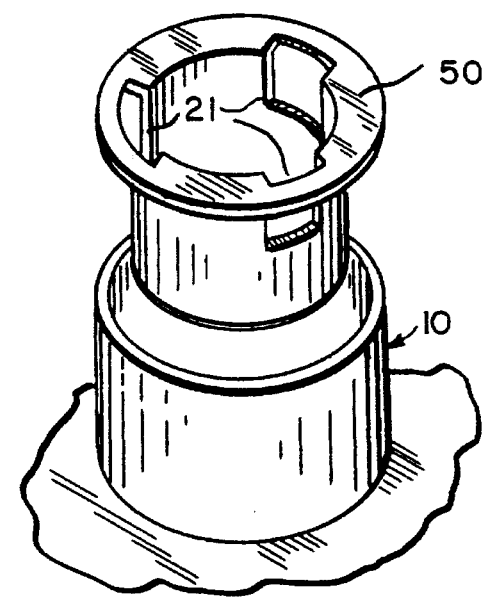
FIG. 2 is an exploded isometric view of the apparatus shown in FIG. 1.
Figure 3:
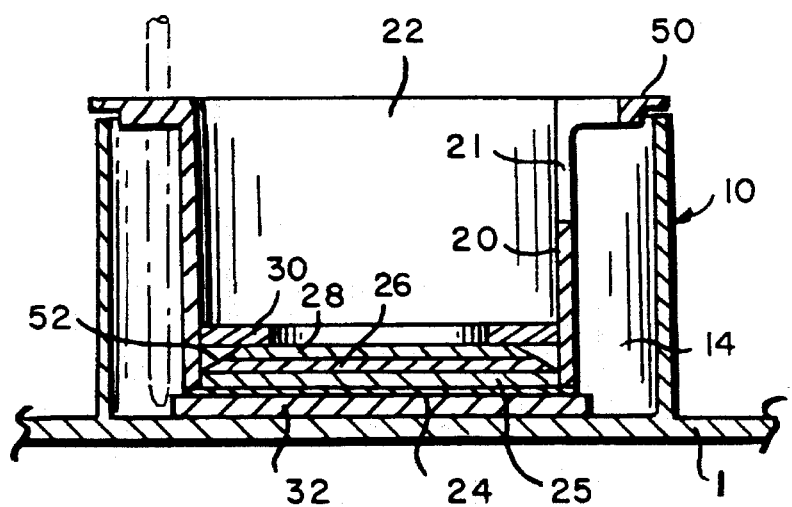
FIG. 3 is section along 3—3 through the apparatus shown in FIG. 1.

Referring to the drawings, FIGS. 1–3 illustrate one embodiment of an apparatus for determining the interaction of skin and one or more agents by use of skin tissue equivalents in accordance with the present invention, wherein multiple containers 10,22 having tissue equivalents of the present invention disposed therein are provided in a base or holder. The apparatus shown in FIGS. 1–3 is also provided with a cover means 2. In some embodiments a covering (not shown) is provided for each container 10,20. The covering is selected from any biocompatible material which will hold a seal on the container. Acceptable covering materials include foils and barrier films which may be sealed to the apparatus by means of an adhesive or heat. A heat sealable polyester film is particularly useful in the practice of the present invention.

The containers for the tissue equivalents comprise an outer container 10 and an inner container 20. The inner container 20 is provided with a rim 50 to provide means for positioning the inner container 20 in the outer container 10 thereby defining an outer area 14 and an inner area 22. The inner container 20 is provided with a skin tissue equivalent 26, 28 disposed on hydratead collagen gel 25 which is in turn disposed adjacent a permeable member 24. The permeable member is sealably attached to the inner container 20 to form the bottom surface thereof. The skin tissue equivalent comprises two layers 26, 28, layer 28 comprising an epidermal layer, layer 26 comprising a dermal layer. In some embodiments, a sealing member 30 provides a seal between the inner wall of the inner container 20 and the skin equivalent 26, 28 and covers the perimeter of hydrated collagen gel 25 in the case where the outer edge of the tissue equivalent 26, 28 is positioned inward of hydrated collagen gel 25. In the embodiments pictured in the Figures, the container 10 is provided with an opening 21 which provide access to the outer area 14.

The apparatus depicted in FIG. 3 is further provided with a absorbent member 32. In yet other embodiments, the outer chamber 14 may have a gel, not shown, disposed therein.

Figure 4:
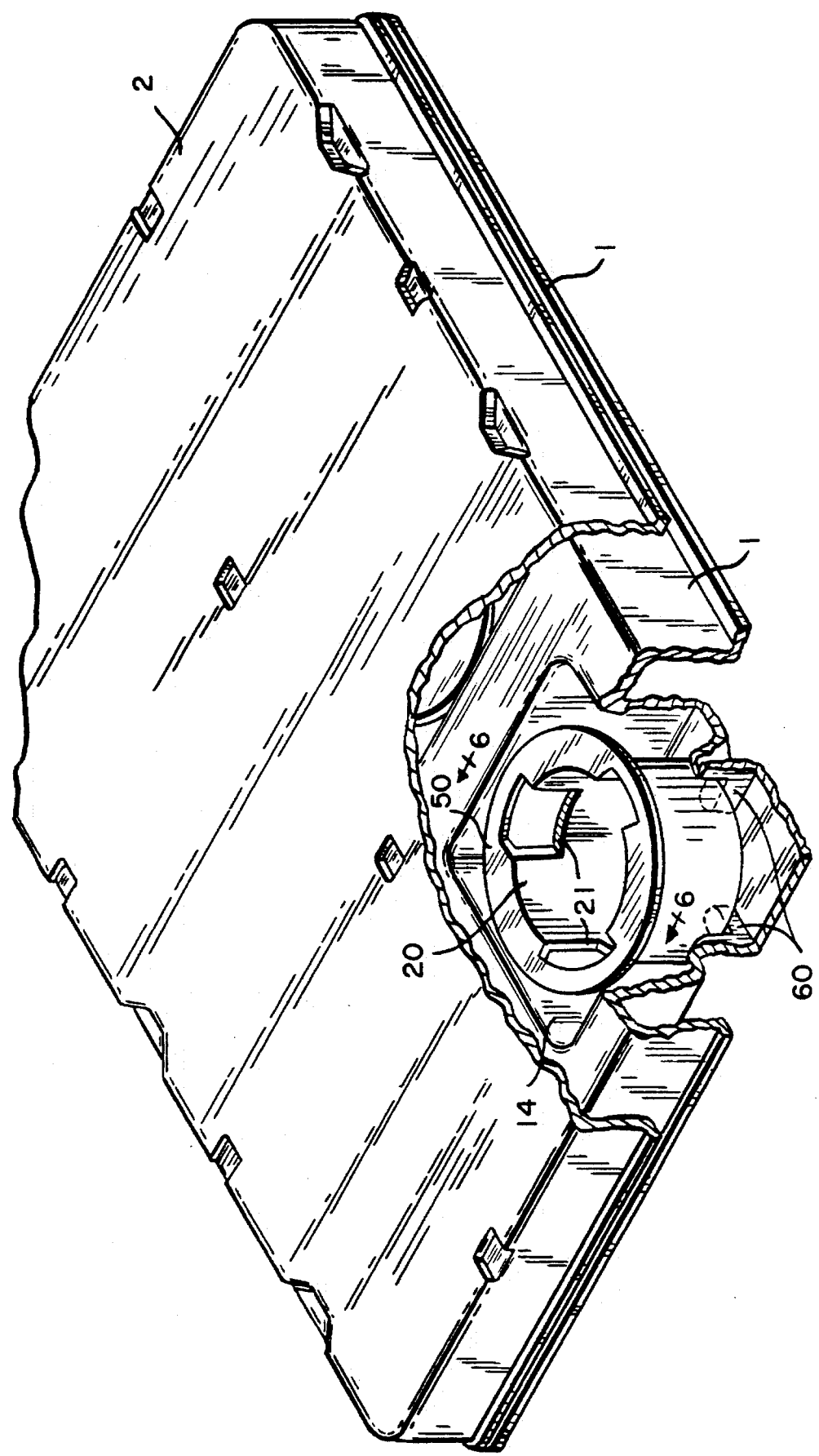
FIG. 4 is an isometric view, partially broken away, of another apparatus in accordance with the present invention.
Figure 5:
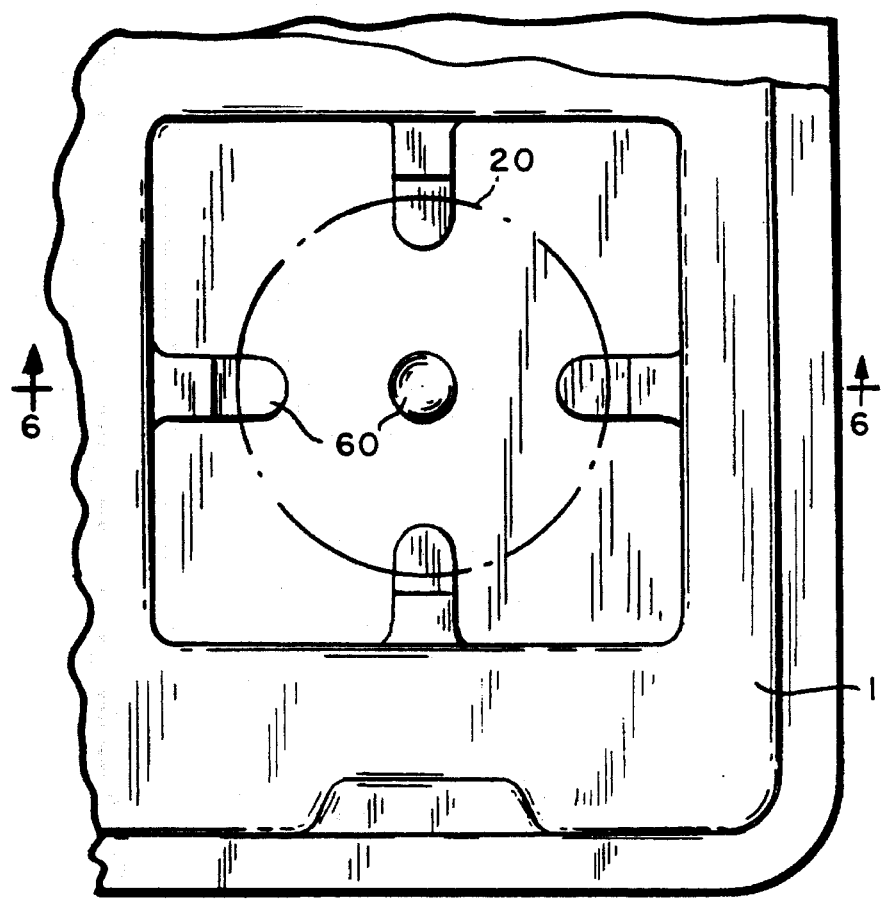
FIG. 5 is an exploded view from above of the apparatus shown in FIG. 4.
Figure 6:
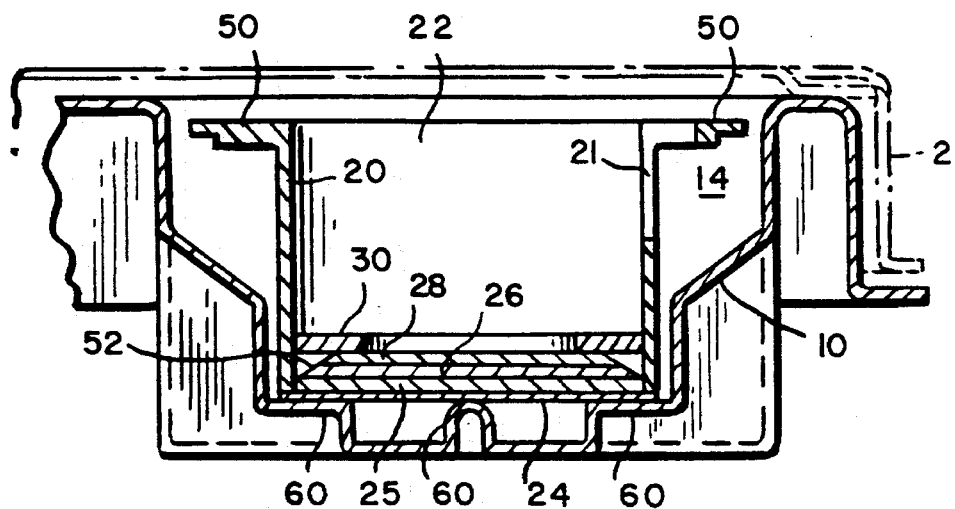
FIG. 6 is an exploded section along 6—6 through the apparatus shown in FIG. 4.

FIGS. 4–6 illustrate another embodiment of an apparatus for determining the interaction of tissue and one or more agents by use of tissue equivalents in accordance with the present invention. Elements similar to those in other described embodiments are indicated by the same numeral. In this embodiment, the outer well 10 is square and is provided with elevated sections 60 in the bottom on which the inner container 20 may be positioned. The outer well 10 rather than projecting upwardly from the bottom of the apparatus is formed as a pocket from the top of the apparatus.

The outer well 10 is provided with nutrient medium for the tissue equivalent. Such media are known in the art. Preferred serum free nutrient media are disclosed in copending U.S. patent application Ser. No. 361,041. The volume of medium must be selected to fill the outer container 14 to an appropriate level so as not to build up a head of pressure which would force the medium through the permeable member 24, the hydrated collagen gel 25, the tissue equivalent 26, 28, into the inner container 20.

In some embodiments of the present invention, the outer container 10 is provided with an absorbent member 32 which is disposed in the outer container 10 so as to contact the outer surface of the permeable member 24. The absorbent member 32 must be compatible with living tissue equivalents. Preferred materials for the absorbent member include cotton, polyester and rayon. A particularly preferred material is absorbent cotton. In general, it is preferred that the absorbent member be free of additives such as detergents.

In other embodiments of the present invention, the outer well 10 is provided with a gel (not shown), such as agarose, which serves to trap the medium. Because the agarose gel can be added up to just below the level of the openings 21, a greater amount of nutrient medium is made available to the tissue equivalent and nutrient supply to the tissue equivalent 26, 28 is not exhausted as quickly. The use of such gels provides benefits in storing and shipping the apparatus of the present invention in terms of minimizing leakage of the media and resultant potential contamination of the tissue equivalent.

The outer 10 and inner 20 containers may be made of any desired material which does not react with or have an undesirable effect on the components of the assay, including the tissue equivalent. For example, the casting mixture for the living tissue equivalent must not adhere to the walls of the inner container during contraction so as to interfere with formation of the tissue equivalent.

It has been found that methods used to sterilize the inner container 20 may impact adherence of the tissue equivalent. For example, the forming tissue will adhere to polystyrene, one preferred material for the inner container, when it is sterilized by electron beam but not when it is sterilized by ethylene oxide. In contrast, K-RESIN® butadiene-styrene polymer, an alloy of polystyrene and butadiene and a particularly preferred material for the inner container, may be sterilized by electron beam without causing the forming tissue equivalent to adhere. (K-RESIN® butadiene-styrene polymer is a trademark of Phillips Petroleum.) In some embodiments, it is desirable that the containers be made so that the tissue equivalent is visible through the container, e.g., through the walls of the container or through a window in the container. Preferred materials for the container 10 include polystyrene and PETG.

The inner container 20 may be of any shape and volume which will accommodate the size and shape of the desired tissue equivalent. The dimensions of the container will again depend upon the size and shape of the desired tissue equivalent and the desired assay volumes. For example, a container having an outer diameter of about 25 mm and a volume of about 5 ml is useful in practicing the present invention. In the embodiment shown in FIGS. 1–3, multiple containers are provided in a base or holder.

The permeable member 24 must have sufficient strength to support the acellular, hydrated collagen gel 25 and the tissue equivalent 26, 28. Porous membranes are useful in the practice of the present invention. The pore size of such membranes is selected so as to provide attachment for the acellular, hydrated collagen gel 25. Preferred membranes are hydrophylic, have a thickness of about 1 to 10 mm, and pore diameters ranging from about 1 to about 10 μ. Preferred materials for the permeable member 24 include polycarbonate. A particularly preferred permeable member is a polycarbonate membrane, preferably free of wetting agents, commercially available from Nuclepore and having a pore size of about 3 to 10 μ.

The sealing means 30 may be made of any material which is inert to the conditions of the assay and the tissue equivalents being used, as well as provides a good seal between the inner container 20 and the tissue equivalent. Preferred materials include polyethylene, TEFLON® PTFE Polytetrafluoroethylene, a trademark of E.I. Du Pont de Nemours and Company, polycarbonate and nylon. The sealing means is especially useful where it is desired to keep the contents of the outer container separated from any solution or substance applied to the epidermis 25, e.g., when measuring the diffusion or permeation of a substance through a tissue equivalent.

Both the tissue equivalents and the acellular, hydrated collagen gel in accordance with the present invention may be prepared using collagen derived from skin and tendon, including rat tail tendon, calf skin collagen, and calf extensor tendon. Other sources of collagen would be suitable. A particularly preferred collagen composition derived from calf common digital extensor tendon and methods of deriving such collagen compositions are disclosed in co-pending U.S. patent application Ser. No. 07/407,465 filed on even date herewith, the disclosure of which is incorporated herein by reference.

In one method of the present invention, an acellular, hydrated collagen gel 25 is prepared from a collagen composition comprising collagen at about 0.5 to 2.0 mg/ml, preferably about 0.9 to 1.1 mg/ml and nutrient media. This collagen composition is added to the inner container 20 and maintained under conditions which permit the collagen composition to set and form an acellular, hydrated collagen gel of suitable dimensions, typically about 1 to 5 mm thick, a preferred thickness range being about 2 to about 3 mm. An acellular, hydrated collagen gel 25 is preferably thick enough so that a portion remains acellular as cells migrate from the tissue equivalent into an acellular, hydrated collagen gel and thin enough so that the tissue equivalent is not undesirably removed from the nutrient source provided in outer container 10.

A dermal equivalent is next cast on an acellular, hydrated collagen gel using procedures in accordance with the Patents and as described hereinafter. A casting mixture containing collagen and fibroblasts is added to inner container 20 over an acellular, hydrated collagen gel 25 and maintained under conditions which enable the tissue equivalent to form. As the tissue equivalent forms on an acellular, hydrated collagen gel 25, it contracts radially. However, an acellular, hydrated collagen gel 25 prevents excessive radial contraction of the tissue equivalent without the need of mechanical restraining means such as textured metals and plastics or VELCRO® Hook and Loop Fasteners, a trademark of Velcro Corporation.

Typically, the sides of the tissue equivalent 26 slope towards the outer periphery of hydrated collagen gel 25 to form a mesa as shown in FIGS. 3 and 6 at 52. The tissue equivalent 26 is now seeded with epithelial cells to form the epidermal layer 28. The epidermal cells are seeded in culture medium at a concentration of at about $0.3 \times 10^6$ to $30 \times 10^6$ cells/ml. The volume of epidermal cells seeded will depend upon the size of the mesa.

The concentration of collagen, the number of cells and the volume of the casting mixture can be controlled to optimize the diameter and thickness of the living tissue equivalent. The casting mixture comprises cells at a concentration of about 1.25 to $5 \times 10^4$ cells/ml and collagen at about 0.5 to 2.0 mg/ml in a nutrient medium. A preferred cell concentration is about $2.5 \times 10^4$ cells/ml. It has been found that the ratio of the volume of the casting mixture for the tissue equivalent to the volume of the casting mixture for the acellular, hydrated collagen gel has an effect upon cell viability and differentiation. Useful ratios, v/v, of tissue equivalent casting mixture to collagen gel casting mixture are about 3:1 to 1:3. A preferred ratio wherein the cell concentration in the collagen lattice is at about $2.5 \times 10^4$ cells/ml is 3:1.

The invention will be further understood with reference to the following examples, which are purely exemplary in nature, and are not meant to be utilized to limit the scope of the invention.

Materials used in the following examples were obtained from the sources indicated in the examples or made in accordance with the indicated publications. Sterile procedures were used throughout the Examples. The tissue equivalents were maintained under 10% $CO_2$ in the incubator and sterile procedures were used throughout.

EXAMPLE I

Preparation of Skin Tissue Equivalent Test Systems

A. An apparatus similar to that shown in FIG. 4. was used in conducting the work described hereinafter. The cover is removed for conducting operation but is otherwise kept in place to maintain sterility. Pertinent information regarding the apparatus is listed below:

| | |
|---|---|
| Outer container 10: | diameter 38 mm |
| | capacity 35 ml |
| Inner container 20: | diameter 24 mm |
| | capacity 4 ml |
| Permeable member 24: | Polycarbonate membrane from Nuclepore, pore size 3μ, thickness 5μ. |

B. An acellular, hydrated collagen gel was formed on the permeable member 24 as follows:

| (1) Premix: | |
|---|---|
| 10X MEM | 16.2 ml |
| L-glutamine (200 mM) | 1.6 ml |
| gentamycin (50 mg/ml) | 0.2 ml |
| Fetal bovine serum | 18.0 ml |
| Sodium bicarbonate (71.2 mg/ml) | 5.0 ml |

The stock solutions were mixed at 37° C., combining in the above sequence, and stored at 4° C. for approximately 30 min. in 50 ml. tube (not gassed). (2) 27.8 g of a 1 mg/ml collagen solution (extracted by acid from calf common digital extensor tendon) in 0.05% v/v acetic acid, was weighed out into a 50 ml tube and stored 4° C. for 30 min.

(3) 8.2 ml of the pre-mix described above and 4 ml of DMEM complete (containing 10% FBS, 4mM L-glutamine, 50 µg/ml gentamycin) was added (and 1 ml aliquots pipetted into the inner container 20 and allowed to gel in a hood.

C. Tissue equivalents were cast with human dermal fibroblasts and seeded with human epidermal (epithelial) cells as described below. A general description of procedures and reagents may also be found in the Patents and copending application Ser. No. 07/361,041, filed Jun. 5, 1989.

(1) Casting mixture:

8.2 ml of the pre-mix described above was added to 27.8 g of a 1 mg/ml collagen solution in 0.05% v/v acetic acid, as described in step A(2) above, and 4 ml of human dermal fibroblasts ($2.5 \times 10^5$ cells/ml) were combined. 3 ml aliquots were pipetted into the container 20 over the acellular, hydrated collagen gel formed in step B(2) above and allowed to gel. 4.5 ml DMEM complete was added to the outside container 20 and then incubated at 36° C./10% $CO_2$ typically for 4–8 days.

The following medium was used:

| Components | mSBM |
| --- | --- |
| Hydrocortisone | 1.1 µM |
| Insulin | 5 µg/ml |
| Transferrin | 5 µg/ml |
| Triiodothyronine | 20 pM |
| Ethanolamine | $1 \times 10^{-4}$ M |
| O-phosphorylethanolamine | $1 \times 10^{-4}$ M |
| Adenine | 0.18 mM |
| Progesterone | $2 \times 10^{-9}$ M |
| Selenium | $5.26 \times 10^{-8}$ M |
| Bovine Serum | 0.3% |
| Epidermal Growth Factor | 10 ng/ml |
| Calcium Free DMEM | 75% |
| Ham's F-12 | 25% |

Two other media used were identical with mSBM except as noted below:

| | cSBM | mainSBM |
| --- | --- | --- |
| Progesterone | 0 | 0 |
| Bovine Serum | 2.0% | 1% |
| Epidermal Growth Factor | 1 ng/ml | 1 ng/ml |
| Calcium Free DMEM | 50% | 50% |
| Ham's F-12 | 50% | 50% |

In some instances calcium chloride was added to the media at 1.8 mM. This is indicated as medium plus calcium, e.g., mSBM plus calcium.

D. Epidermalization was initiated at 6 days after casting the tissue equivalent.

(1) Epidermalizing

The medium of step C above was removed from both the inside 20 and outside 10 containers. A 50 µl suspension of human epidermal cells ($3.33 \times 10^6$ cells/ml) was placed on the tissue equivalent formed above in step C above. The container was then incubated at 36° C. and 10% $CO_2$ for 4 hours. 12.0 ml of mSBM was then added to the outside chamber and 4 ml to the well. The apparatus was then returned to the same incubator.

(2) Differentiating

At 2 days post epidermalization the medium was removed and replaced with mSBM plus calcium.

(3) Airlifting

At 5 days post epidermalization, the following procedure was performed: Medium was removed from inside and outside chambers. The inner container 20 was removed and two volumes cSBM plus calcium soaked cotton pads were positioned in the bottom of the outer chamber 10 and 9.0 ml of cSBM plus calcium added. The inner container 20 was then replaced and the apparatus incubated at 35.5° C. and 10% CO2.

(4) Maintaining

Every 4 days the medium was removed and replaced with fresh mainSBM plus calcium.

EXAMPLE II

Preparation of Test Systems Incorporating Agarose

A 2% agarose solution in water was sterilized by autoclaving, cooled to 40° C. and mixed with an equal volume of 2 concentrated mainSBM. The absorbent cotton pads were removed and 13 ml of the mixture was poured into the outer area 14, allowed to set at 36° C. (10% $CO_2$) and the apparatus returned to the incubator for storage prior to shipment.

It is understood that the examples and embodiments described herein are for illustrative purposes only, and that various modifications or changes in light thereof that will be suggested to persons skilled in the art are to be included in the spirit and purview of this application and the scope of the approved claims.

What is claimed is:

1. A method of producing a tissue equivalent in an apparatus, the apparatus comprising at least one container for the tissue equivalent, the container comprising:

(i) an inner well comprising one or more walls;

(ii) a permeable membrane defining the bottom of the inner well; and (iii) an outer well within which the inner well is disposed, the outer well being arranged for containing a nutrient medium in contact with the permeable membrane, wherein, the method comprises:

(a) applying a solution comprising collagen in the absence of cells to the permeable membrane of the apparatus;

(b) maintaining the solution of step (a) under conditions which permit the collagen solution to gel and to form a first collagen gel on the permeable membrane;

(c) applying a mixture comprising collagen and at least one contractile agent to the first collagen gel; and (d) forming a tissue equivalent by maintaining the mixture of step (c) under conditions which permit (i) the mixture to gel and form a second collagen gel on the first collagen gel, and (ii) radial contraction of the second gel by the contractile agent to form a contracted collagen lattice on the first collagen gel, wherein the radial contraction is controlled by the first collagen gel.

2. The method of claim 1, wherein the contractile agent comprises fibroblast cells and the outer well contains a nutrient medium.

3. The method of claim 2, wherein the mixture of step (c) contains fibroblast cells at a concentration of about $1.25 \times 5 \times 10^4$ cells/ml and collagen at about 0.5 to 2.0 mg/ml.

4. The method of claim 1, wherein the solution of step (a) comprises collagen at a concentration of about 0.5 to 2.0 mg/ml.

5. The method of claim 4, wherein the mixture of step (c) and the solution of step (a) are used at a ratio of about 3:1 to 1:3, volume:volume.

6. The method of claim 1, wherein an absorbent member is disposed adjacent the permeable member opposite the first collagen gel.

7. The method of claim 6, wherein the absorbent member comprises a fibrous pad or a gel.

8. The method of claim 7, wherein the fibrous pad is cotton.

9. The method of claim 1, wherein a gel comprising agarose is disposed in the outer well of the apparatus and in contact with the permeable member.

10. The method according to claim 1, wherein the apparatus further comprises a cover means, the means being removably sealable to the inner or outer well.

11. The method according to claim 1, wherein the inner well is provided with at least one opening, the opening communicating with the region defined by the outer container.

12. The method according to claim 1, wherein the inner container comprises butadiene-styrene polymer.

13. The method according to claim 1, wherein the outer well comprises a nutrient medium and further comprising step (e) of disposing human epidermal cells on the tissue equivalent formed in step (d) and maintaining the tissue equivalent and epidermal cells under conditions which permit epidermalization to form a skin tissue equivalent, 14. The method of producing a skin tissue equivalent according to claim 13, wherein the outer well comprises a nutrient medium and further comprising step (f) of providing the outer well with at least one cotton pad to provide contact between the cotton pad and the permeable member, and maintaining the epidermalized tissue equivalent of step e under conditions which permit cornification.

15. The method according to claim 1, wherein the first collagen gel is about 1 to 5 mm thick.

16. The method according to claim 15, wherein the first collagen gel is about 2 to 3 mm thick.

17. The method of claim 1, wherein the permeable membrane is a hydrophilic membrane.

18. The method of claim 17, wherein the hydrophilic membrane has a pore diameter from about 1 to about 10 μ.

19. The method of claim 18, wherein the hydrophilic membrane is a polycarbonate membrane having a pore size of about 3 to 10 μ.

20. A tissue equivalent produced by the method of claim 1.

21. A skin tissue equivalent produced by the method of claim 13.

22. A skin tissue equivalent produced by the method of claim 14.

* * * * *